United States Patent [19]

Ichijima et al.

[11] 4,308,343
[45] Dec. 29, 1981

[54] PROCESS AND MATERIAL FOR FORMING COLOR PHOTOGRAPHIC IMAGE

[75] Inventors: Seiji Ichijima; Nobuo Furutachi, both of Kanagawa, Japan

[73] Assignee: Fuji Photo Film Co., Ltd., Minami-ashigara, Japan

[21] Appl. No.: 184,453

[22] Filed: Sep. 5, 1980

[30] Foreign Application Priority Data

Sep. 5, 1979 [JP] Japan .................. 54-114005

[51] Int. Cl.$^3$ .............................................. G03C 7/00
[52] U.S. Cl. .................................. 430/387; 430/558; 430/505
[58] Field of Search .............. 430/558, 557, 555, 387, 430/505

[56] References Cited

U.S. PATENT DOCUMENTS

| | | | |
|---|---|---|---|
| 2,575,182 | 11/1951 | Martin | 430/558 |
| 2,865,748 | 12/1958 | Feriak et al. | 430/558 |
| 4,061,498 | 12/1977 | Monbaliu et al. | 430/555 |
| 4,062,683 | 12/1977 | Monbaliu et al. | 430/555 |
| 4,076,533 | 2/1978 | Ota et al. | 430/555 |

Primary Examiner—J. Travis Brown
Attorney, Agent, or Firm—Sughrue, Mion, Zinn, Macpeak and Seas

[57] ABSTRACT

A process for forming a color photographic image comprising processing a silver halide color photographic light-sensitive material in the presence of a magenta coupler represented by the formula (I)

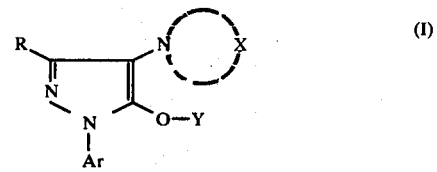

wherein R represents an acylamino group, an anilino group or a ureido group; Ar represents a substituted or unsubstituted aryl group; X represents a non-metallic divalent group forming a saturated or unsaturated 5-membered or 6-membered heterocyclic ring together with the nitrogen atom; and Y represents an acyl group or a sulfonyl group.

The 2-equivalent magenta coupler represented by the formula (I) is stable to chemicals and has a good solubility to an organic solvent which is employed to incorporate couplers into a photographic light-sensitive material. A photographic light-sensitive material comprising a support having thereon at least one silver halide emulsion layer containing the 2-equivalent magenta coupler represented by the formula (I) is also disclosed.

25 Claims, No Drawings

PROCESS AND MATERIAL FOR FORMING COLOR PHOTOGRAPHIC IMAGE

BACKGROUND OF THE INVENTION

1. Field of the Invention

This invention relates to a color image forming process and a silver halide photographic light-sensitive material utilizing a novel 2-equivalent magenta color-forming coupler (also referred to herein simply as the "magenta coupler").

2. Description of the Prior Art

It is known that, upon color development of a silver halide color photograhic material, an oxidized aromatic primary amine color developing agent reacts with a coupler to form an indophenol, indoaniline, indamine, azomethine, phenoxazine, phenazine or like dye, thereby forming color images. In such a system, color reproduction is usually based on subtractive color photography, and silver halide emulsions selectively sensitive to blue, green and red light, respectively, and yellow, magenta and cyan color image-forming compounds which are in a complementary color relation to the sensitivity of the respective emulsions are employed. For example, acylacetanilide or dibenzoylmethane couplers are generally used for the formation of a yellow color image; pyrazolone, pyrazolobenzimidazole, cyanoacetophenone and indazolone couplers are generally used for the formation of magenta color images, and phenolic couplers (e.g., phenols and naphthols) are generally used for the formation of cyan color images.

In one of the most preferred embodiments of color photographic light-sensitive materials, dye image-forming couplers are added to silver halide emulsions. Couplers added to emulsions must be rendered nondiffusible (or diffusion-resistant) in a binder matrix of the emulsions.

Most conventional color image-forming couplers are 4-equivalent couplers. That is, the development of 4 mols of silver halide as an oxidizing agent is theoretically necessary to form 1 mol of dye through the coupling reaction. On the other hand, 2-equivalent couplers are also known, having an active methylene group substituted with a group (often referred to as a "coupling-off" group) eliminatable upon oxidative coupling of the coupler with an oxidation product of an aromatic primary amine developing agent. Such 2-equivalent couplers require the development of only 2 mols of silver halide to form 1 mol of dye. Since 2-equivalent couplers require only one-half the silver halide as compared with conventional 4-equivalent couplers to form a dye, their use enables rapid processing of light-sensitive materials due to the thinness of the light-sensitive layer, improvement of the photographic properties due to a reduction in film thickness, and results in economic advantages.

Several approaches have thus far been suggested to produce 2-equivalent 5-pyrazolone couplers (primarily for use as magenta-forming couplers). For example, the substitution of the 4-position of a pyrazolone with a thiocyano group is described in U.S. Pat. Nos. 3,214,437 and 3,253,924, with an acyloxy group is described in U.S. Pat. No. 3,311,476, with an aryloxy group is described in U.S. Pat. No. 3,419,391, with a 2-triazolyl group is described in U.S. Pat. No. 3,617,291, and with a halogen atom is described in U.S. Pat. No. 3,522,052.

However, in using these 4-position substituted pyrazolone couplers, there are disadvantages, e.g., serious color fog may result; the reactivity of the couplers may be unsuitable; the couplers may be chemically so unstable that they are converted to materials incapable of color formation with the lapse of time; or synthesis of the couplers is often difficult.

Also, it has hitherto been known to substitute the 4-position of a 5-pyrazolone with an alkylthio group, an arylthio group or a heterocyclic ring thio group, as described in U.S. Pat. No. 3,227,554. However, with many of these known thio-substituted pyrazolone compounds, the reactivity with the oxidation product of an aromatic primary amino color developing agent is unsuitable and, further, they are difficult to employ in ordinary color light-sensitive materials due to the strong photographic action of the mercapto compound produced as a result of the coupling reaction. In addition, the chemical stability of these couplers is not generally satisfactory.

Further, pyrazole type magenta couplers having an arylthio group or an alkylthio group at the 4-position thereof and an acyloxy group or a sulfonyloxy group at the 5-position thereof are disclosed in Japanese Patent Application (OPI) No. 80744/79 (the term "OPI" as used herein refers to a "published unexamined Japanese patent application"). These 4-position thio-substituted pyrazole compounds show improved stability to formalin gas in comparison with the corresponding 4-equivalent couplers. Although these pyrazole compounds have good stability to a certain degree in comparison with the corresponding 4-position thio-substituted pyrazolone compounds, they are still insufficient for practical use. Therefore, compounds having higher stability have been desired. Also, these known compounds show only small improvements in the increase of sensitivity. Furthermore, these compounds have certain restrictions to utilize in ordinary color light-sensitive materials since the problems such as effects to other photographic layers, contamination of color development processing solutions, etc., due to the photographic action of the mercapto compound produced as a result of the coupling reaction are accompanied.

Recently, 2-equivalent 5-pyrazolone magenta couplers having a heterocyclic substituent at the 4-position thereof have been disclosed in some patents. For example, an imidazolyl group and a derivative thereof, a 1,2,4-triazolyl group and a derivative thereof and a 1,2,3-triazolyl group and a derivative thereof are described in German Patent Application (OLS) No. 2,536,191, and a 1,2,4-triazolyl group and a derivative thereof are described in German Patent Application (OLS) No. 2,651,363.

The compounds described in the above-mentioned patents show good color-forming properties, and thus satisfy one of the characteristics required of 2-equivalent magenta couplers. However, those couplers having an imidazolyl group or a 1,2,4-triazolyl group still also have some disadvantages. For example, their use is accompanied by a decrease in the sensitivity of the silver halide due to interaction with the silver halide (for example, by adsorption onto the light-sensitive center of silver halide, etc.) and the chemical stability of these couplers is not satisfactory. Furthermore, many 2-equivalent 5-pyrazolone magenta couplers having a heterocyclic substituent at the 4-position thereof have a low solubility to an organic solvent and thus, in certain case, it is incapable of dispersing these couplers in a silver halide emulsion. Therefore, the increase in solubility of couplers is recently one of the important problems with respect to 2-equivalent magenta couplers as well as the improvement in photographic properties.

SUMMARY OF THE INVENTION

Therefore, an object of the present invention is to provide a novel 2-equivalent magenta coupler in which the coupling position (i.e., the 4-position) is substituted with a group eliminatable upon coupling with an oxidation product of an aromatic primary amine developing agent.

Another object of the present invention is to provide a color photographic light-sensitive material having higher sensitivity and excellent color forming property same as that possessed just after its production even storage for a long period of time using a stable coupler.

A further object of the present invention is to provide a coupler which has a good solubility to an organic solvent and thus which is suitable for use in an oil soluble process in which the coupler is dispersed in an aqueous medium as a fine colloidal particle and added to an emulsion.

A still further object of the present invention is to provide a process for reducing the amount of silver halide in a photographic emulsion layer by using a novel 2-equivalent magenta color image-forming coupler therein, thus, allowing for thinner emulsion layers and improving the sharpness of color images.

A still further object of the present invention is to provide a color photograph having a fast color image by using a novel magenta color image-forming coupler.

It is also an object of the present invention to provide a color photographic light-sensitive material having high sensitivity using a novel 2-equivalent magenta coupler.

It is also an object of the present invention to provide a 2-equivalent magenta coupler showing improved degree of conversion to the dye, having improved resistance to a reduction in coloration due to the attack of chemicals, and having excellent coloration reactivity.

A further object of the present invention is to provide a color photographic light-sensitive material having a silver halide emulsion layer containing a novel magenta color image-forming coupler.

These and other objects of the present invention will become apparent from the following detailed description and examples.

These objects of the invention are attained by a process using a novel photographic coupler represented by the formula (I) described below and, particularly, by using a color photographic light-sensitive material comprising a support having thereon at least one silver halide emulsion layer with at least one of the silver halide emulsion layers containing a novel 2-equivalent magenta coupler represented by the formula (I) described below.

The couplers according to the invention are represented by the formula (I)

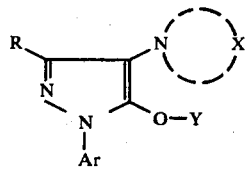

(I)

wherein R represents an acylamino group, an anilino group or a ureido group; Ar represents a substituted or unsubstituted aryl group; X represents a non-metallic divalent group forming a saturated or unsaturated 5-membered or 6-membered heterocyclic ring together with the nitrogen atom; and Y represents an acyl group or a sulfonyl group.

DETAILED DESCRIPTION OF THE INVENTION

Examples of the acylamino groups for R include an aliphatic acylamino group having 2 to 30 carbon atoms or an aromatic acylamino group having 6 to 32 carbon atoms which may be substituted with a halogen atom, an acylamino group, an alkoxy group, an aryloxy group, an aryl group, a sulfonamido group, a sulfamoyl group, an alkoxycarbonyl group, an imido group, a cyano group, a carboxy group, an alkylcarbonyl group, an aryloxycarbonyl group, a sulfo group, an acyloxy group, a carbamoyl group, a ureido group, a urethane group, a heterocyclic group, an alkylsulfonyl group, an arylthio group, an alkylthio group, an anilino group, a hydroxy group, an arylsulfonyl group, etc., such as, for example, an acetamido group, a benzamido group, a 3-[α-(2,4-di-tert-amylphenoxy)butyramido]benzamido group, a 3-[α-(2,4-di-tert-amylphenoxy)acetamido]benzamido group, a 3-[α-(3-pentadecylphenoxy)butyramido]benzamido group, a γ-(2,4-di-tert-amylphenoxy)butyramido group, an α-(3-pentadecylphenoxy)butyramido group, etc.

The anilino groups for R may be substituted with a straight or branched chain alkyl, alkenyl, aralkyl or aryl group, and the same groups as described above for the acylamino group, and have 6 to 32 total carbon atoms (inclusive of the anilino moiety). Representative examples include an anilino group, a 2-chloroanilino group, a 2,4-dichloroanilino group, a 2-chloro-5-tetradecanamidoanilino group, a 2-chloro-5-(2-octadecenylsuccinimido)anilino group, a 2-chloro-5-[α-(3-tert-butyl-4-hydroxy)tetradecanamido]anilino group, a 2-chloro-5-tetradecyloxycarbonylanilino group, a 2-chloro-5-(N-tetradecylsulfamoyl)anilino group, a 2,4-dichloro-5-tetradecyloxyanilino group, etc.

The ureido groups for R may be substituted by the same groups as above-described acylamino group. Representative examples include a 3-[(2,4-di-tert-amylphenoxy)acetamido]phenylureido group, a phenylureido group, a methylureido group, an octadecylureido group, a 3-tetradecanamidophenylureido group, etc.

The aryl group represented by Ar may have one or more substituents. Examples of the substituents include, for example, an alkyl group, an alkenyl group, a cycloalkyl group, an aralkyl group, a cycloalkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group, a mercapto group, etc. A phenyl group in which at least one of the ortho-position is substituted with an alkyl group, an alkoxy group or a halogen atom is preferably used for Ar, since when such a coupler remains in a color photograhic material after development, less coloration due to the action of light or heat occurs.

The substituent —O—Y at the 5-position of the pyrazole represented by formula (I) is represented in more detail by the formula (II) or (III)

wherein $R_1$ represents an alkyl group having from 1 to 18 carbon atoms, and preferably from 1 to 6 carbon atoms, an alkenyl group, a cycloalkyl group, an aralkyl group, an alkylamino group, a dialkylamino group, an anilino group, an alkoxy group or an aryloxy group, and each of these groups may have one or more substituents. Examples of the substituents include a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group, a mercapto group, etc. In the formula (II), n is 1 or 2.

Preferred examples of the substituents represented by the formulae (II) and (III) are illustrated below.

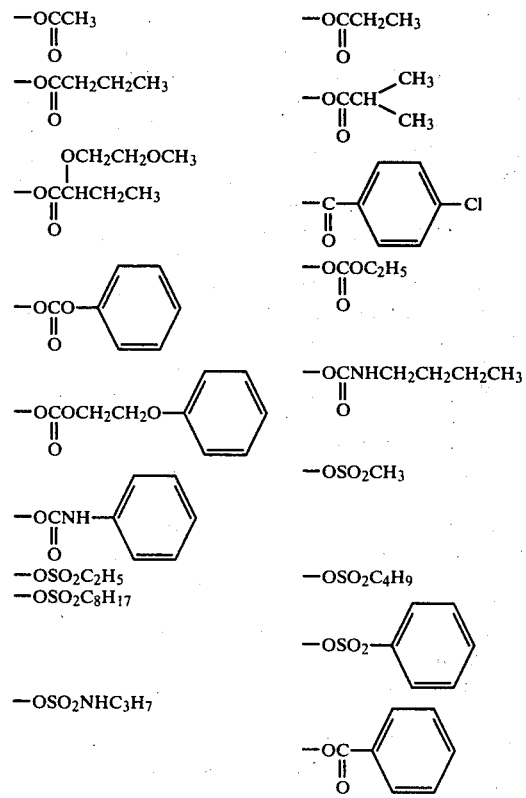

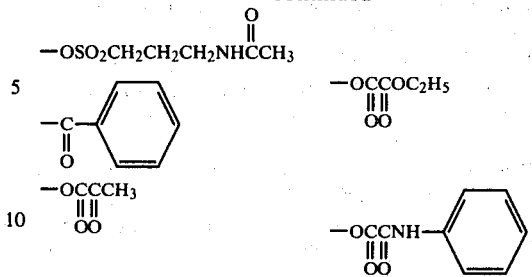

The heterocyclic group substituted at the 4-position of the pyrazole represented by the formula (I) can be a 5-membered ring or a 6-membered ring, and can be saturated or unsaturated. The heterocyclic group is bonded to the coupler moiety through the nitrogen atom and can contain 1 to 3 of a hetero atom such as a nitrogen atom, an oxygen atom or a sulfur atom, as a member to form the ring other than a carbon atom. Examples of the heterocyclic group include, for example, a 1-imidazolyl group, a 1-pyrrolyl group, a 2-isoindolyl group, a 1-indolyl group, a 1,2,4-triazol-1-yl group, a 1,2,3-triazol-1-yl group, a 1-tetrazolyl group, a 1-pyrazolyl group, a 1-indazolyl group, a 1-pyrrolidinyl group, a 2-pyrazolin-1-yl group, a piperidino group, a 1,4-oxazin-4-yl group, a 1,2,3,4-tetrahydroquinolin-1-yl group, a 1,2,3,4-tetrahydroisoquinolin-2-yl group, a 1-indolinyl group, a 2-isoindolinyl group, a 1-piperazinyl group, a 2-pyrrolin-1-yl group, a 1H-pyrazolo[4,5-d]oxazol-1-yl group, a 3-pyrazolin-2-yl group, a 1-pyrazolidinyl group, a 1H-pyrazolo[5,4-d]pyrazol-1-yl group, etc. The heterocyclic ring may have one or more substituents.

Particularly preferred heterocyclic groups substituted at the 4-position of the pyrazole represented by the formula (I) are represented by the following formulae (IV) to (VI)

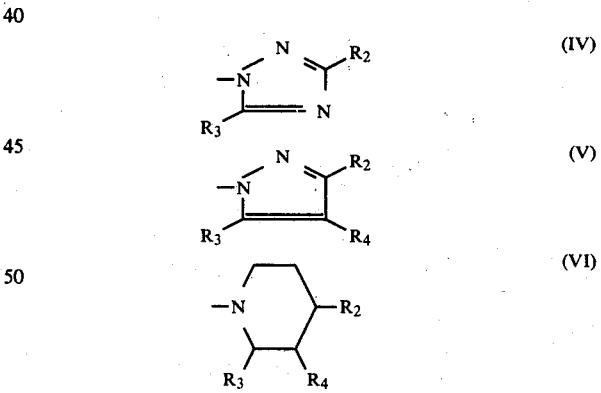

wherein $R_2$, $R_3$ and $R_4$ each represents a hydrogen atom, a halogen atom, a nitro group, a nitroso group, an acylamino group, a sulfonamido group, a urethane group, a diacylamino group, a ureido group, an alkylthio group, an alkylsulfonyl group, an alkoxy group, an alkylcarbonyl group, an alkoxycarbonyl group, a sulfamoyl group, a sulfo group, a hydroxy group, an acyloxycarbonyl group, an arylthio group, an aryloxy group, a carbamoyl group, a cyano group, an anilino group, an arylsulfonyl group or an aryloxycarbonyl group.

Further, $R_2$, $R_3$ and $R_4$ each represents a straight chain or branched chain alkyl group having from 1 to 35 carbon atoms, and preferably from 1 to 22 carbon atoms, an alkenyl group, a cycloalkyl group or an aralkyl group. These groups can have one or more substituents. Examples of the substituents include, for example, a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group, a mercapto group, etc.

Furthermore, $R_2$, $R_3$ and $R_4$ each may represent an aryl group (for example, a phenyl group, an α-naphthyl group, a β-naphthyl group, etc.) or a heterocyclic group (for example, an oxazolyl group, a thiazolyl group, a furyl group, an α-pyridyl group, etc.), and these groups can have as substituents one or more alkyl groups, alkenyl groups, cycloalkyl groups, aralkyl groups, as well as the substituents as described for the alkyl group above.

Furthermore, $R_2$ and $R_4$ together, or $R_3$ and $R_4$ together each represents a divalent group and is bonded each other to form a ring.

Preferred examples of the heterocyclic groups represented by the formulae (IV), (V) and (VI) are illustrated below.

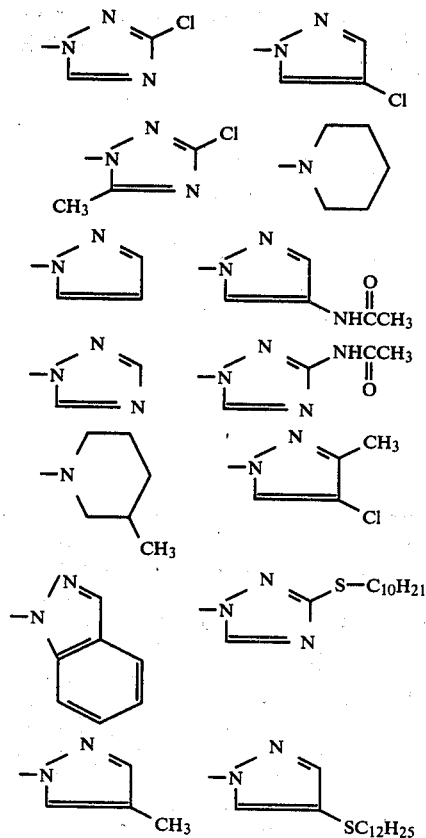

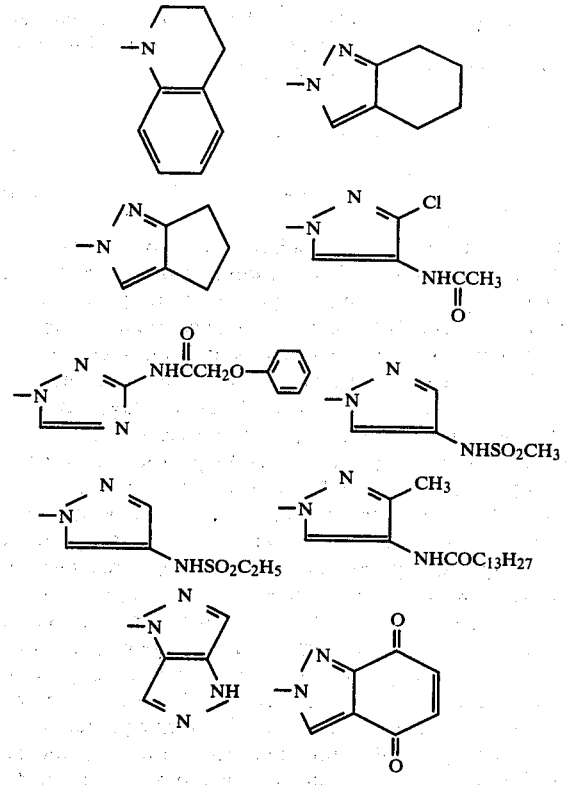

The coupler of the present invention represented by the formula (I) can be a symmetrical or an asymmetrical complex coupler formed by linking two coupler moieties to each other by the substituents of R and Ar or through an R or Ar divalent group.

The magenta couplers used in the present invention provide various properties depending upon the particular R, X, Y and the Ar substituents, and can be employed for various photographic purposes. When at least one of Ar and R contains a hydrophobic residue containing at least 8 carbon atoms, the coupler is rendered non-diffusible when associated with a hydrophilic colloidal layer of a light-sensitive material. Such a coupler can be usefully incorporated in a silver halide emulsion layer.

Couplers having a diffusion-resistant hydrophobic residue in X and containing a water-solubilizing group such as a sulfo group or a carboxy group in at least one of Ar and R provide a diffusible dye through an oxidative coupling reaction with an aromatic primary amine developing agent, although the couplers themselves are non-diffusible. Such couplers which are capable of providing diffusible dyes are useful for diffusion transfer color photography.

The process of forming dye images through oxidative coupling reaction with an aromatic primary amine developing agent can be classified into two types, depending on the manner of addition of the couplers. One type is a so-called incorporated-coupler process wherein the couplers are incorporated in an emulsion layer during the production of a light-sensitive material. The other type is a so-called unincorporated-coupler process wherein the couplers are dissolved in a developer and are supplied, upon development, through diffusion into an emulsion layer.

Couplers for use in an incorporated-coupler type multilayer must be immobilized in an emulsion layer, i.e., must be made diffusion-resistant. Otherwise, couplers would migrate through the light-sensitive material and form color in an unintended emulsion layer having a different color sensitivity, thus seriously degrading the color reproducibility of the light-sensitive material. In order to render the couplers diffusion-resistant, a group having a hydrophobic residue containing from 8 to 32 carbon atoms is introduced into the coupler molecule. Such a residue is called a ballasting group. This ballasting group can be connected to the coupler skeletal structure directly or through an imino bond, an ether bond, a carbonamido bond, a sulfonamido bond, a ureido bond, an ester bond, an imido bond, a carbamoyl bond, a sulfamoyl bond, or the like.

Several specific examples of such ballasting groups are as described in the specific examples of the couplers of the invention.

Typical examples of the ballasting groups include, e.g., an alkyl group, an alkoxyalkyl group, an alkenyl group, an aryl group substituted by an alkyl group, an aryl group substituted by an alkoxy group, a terphenyl group, and the like. These ballasting groups may be substituted by, for example, a halogen atom (e.g., fluorine, chlorine, etc.), a nitro group, a cyano group, an alkoxycarbonyl group, an amido group, a carbamoyl group, a sulfonamido group, etc. Specific examples of the ballasting group include an n-octyl group, a 2-ethylhexyl group, a tert-octyl group, an n-nonyl group, an n-decyl group, an n-dodecyl group, a 1,1-dimethyldecyl group, a 2,2-dimethyldecyl group, an n-octadecyl group, a 2-(n-hexyl)decyl group, an n-octadecyl group, a 9,10-dichlorooctadecyl group, a heptyloxyethyl group, a 2,4-di-tert-amylcyclohexyldodecyloxypropyl group, an oleyl group, a 2,4-di-tert-butylphenyl group, a 2,4-di-tert-amylphenyl group, a 2,4-di-tert-amyl-6-chlorophenyl group, a 3-n-pentadecylphenyl group, a 2-dodecyloxyphenyl group, a 3-heptadecyloxyphenyl group, an o-terphenyl group, a perfluoroheptyl group, etc.

The couplers according to the present invention can be obtained, in general, by the reaction of a magenta coupler having a heterocyclic substituent at the 4-position of the 5-pyrazolone with an appropriate acylating agent (for example, an acid chlorine, an isopropenyl acetate, etc.) with ease. The 5-pyrazolone compounds having a heterocyclic substituent at the 4-position thereof can be synthesized with reference to the methods described, for example, in U.S. Pat. No. 4,076,533, German Patent Application (OLS) Nos. 2,424,467, 2,536,191, 2,813,522 and 2,651,363, British Pat. Nos. 1,516,547 and 1,539,973, etc.

The couplers according to the present invention can be obtained, for example, in accordance with the following Reaction Scheme.

Reaction Scheme

Step 1.

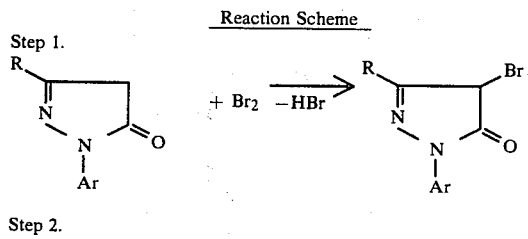

Step 2.

-continued
Reaction Scheme

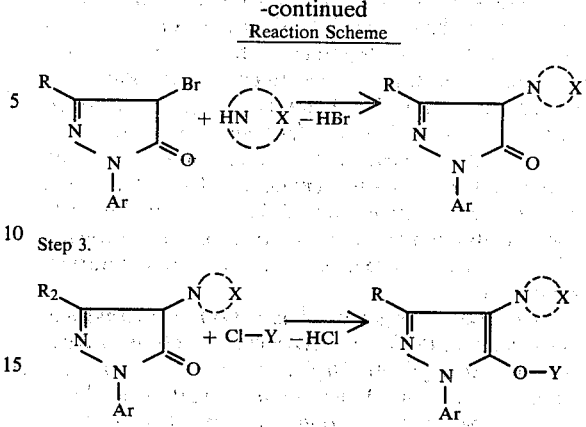

Step 3.

wherein R, Ar, X and Y have the same meaning as defined above. The bromination reaction of Step 1 can be achieved at a temperature of from about $-5°$ to $20°$ C. in various solvents of from about 2 to 20 ml based on 1 g of 5-pyrazolone, such as dichloromethane, chloroform, acetic acid, etc., in the presence of a base such as sodium acetate, triethylamine, etc., or in the absence of a base.

The substitution reaction of Step 2 can be achieved at a temperature of from about $50°$ to $150°$ C. in various solvents such as N,N-dimethylformamide, tetrahydrofuran, acetonitrile, tetrahydrothiophene-S,S-dioxide, toluene, etc., and can be also done according to the solvent-less fusing method at a temperature where starting materials fuse. Since a large excess of heterocyclic rings can be used as a dehydrohalogenation agent, base is not particularly required.

The reaction of Step 3 between the thus-prepared 4-heterocyclic substituted 5-pyrazolone and an acid chloride can be effected at a temperature of from about $0°$ C. to $200°$ C. in various solvents or in the absence of a solvent by melting the reactants, in the presence of a base, such as 1,8-diazabicyclo[5,4,0]-7-undecene-2,6-butidine, sodium acetate, etc., or in the absence of a base. Illustrative preferred solvents include aromatic solvents (such as benzene, toluene, xylene, etc.), aprotic polar solvents (such as dimethylformamide, acetonitrile, etc.), chlorinated hydrocarbon solvents (such as chloroform, carbon tetrachloride, ethylene dichloride, etc.), and the like.

The coupler of the present invention can advantageously be mixed with a solvent dispersion by dissolving the coupler in a water-immiscible organic solvent having a melting point of about $170°$ C. or higher, a low-boiling organic solvent or a water-soluble organic solvent, or in a high-boiling, water-immiscible organic solvent and/or a low-boiling and/or water-soluble organic solvent.

Any of the high-boiling, water-immiscible organic solvents described in U.S. Pat. No. 2,322,027 can be used as a solvent. Preferred solvents include di-n-butyl phthalate, benzyl phthalate, triphenyl phosphate, tri-o-cresyl phosphate, diphenyl mono-p-t-butylphenyl phosphate, monophenyl di-o-chlorophenyl phosphate, dioctyl phthalate, dibutyl sebacate, acetyl tributyl citrate, tri-t-octyl trimellitate, n-nonylphenol, dioctylbutyl phosphate, N,N-diethyllaurylamide, 3-pentadecylphenyl ethyl ether, 2,5-di-sec-amylphenyl butyl ether, and so forth.

Low-boiling organic solvents (having a boiling point of not higher than about 170° C.) or water-soluble organic solvents usable together with or in place of the high-boiling solvents are described in U.S. Pat. Nos. 2,801,171, 2,801,170, 2,949,360, etc. Examples of these organic solvents include the following solvents.

(1) Low-boiling, substantially water-insoluble organic solvents such as methyl acetate, ethyl acetate, propyl acetate, butyl acetate, isopropyl acetate, ethyl propionate, sec-butyl alcohol, ethyl formate, butyl formate, nitromethane, nitroethane, carbon tetrachloride, chloroform, etc.

(2) Water-soluble organic solvents such as methyl isobutyl ketone, β-ethoxyethyl acetate, β-ethoxydiethyl acetate, tetrahydrofurfuryl adipate, Carbitol acetate (diethyleneglycol monoacetate), methoxytriglycol acetate, methyl Cellosolve acetate, acetylacetone, diacetone-alcohol, butyl Carbitol, butyl Cellosolve, methyl Carbitol, methyl ethyl ketone, methanol, ethanol, acetonitrile, dimethylformamide, dioxane, and so forth.

The water content present in the solvent solution should be sufficiently low enough that the solubility of the coupler is not affected.

After production, the low-boiling or water-soluble solvent can be removed from a cooled noodle-like dispersion by air-drying or continuously washing with water as described in, e.g., U.S. Pat. No. 2,801,171.

A homogenizer for emulsification, a colloid mill, an ultrasonic wave emulsifying apparatus, etc., are useful for dispersing oil-soluble couplers. Diffusion-resistant couplers having a carboxylic acid group or a sulfonic acid group in their molecule together with a ballasting group are soluble in a neutral or a weakly alkaline aqueous solution. These couplers can be incorporated into a photographic emulsion by adding an aqueous solution thereof to the photographic emulsion. These couplers are believed to be rendered diffusion-resistant through formation of micelles in a hydrophilic high molecular weight material.

Specific examples of the couplers according to the present invention are illustrated below but the magenta couplers which can be used in the present invention are not to be construed as being limited to these examples.

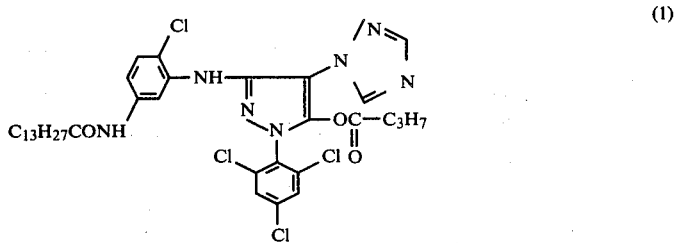

(1)

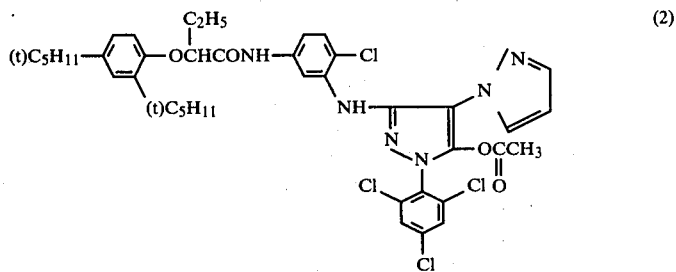

(2)

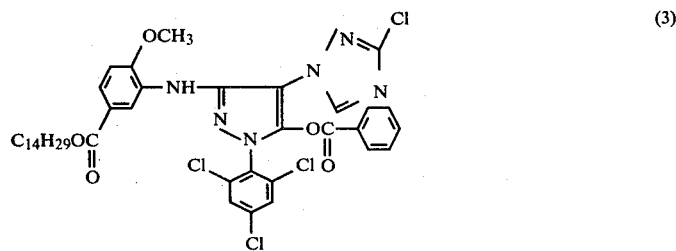

(3)

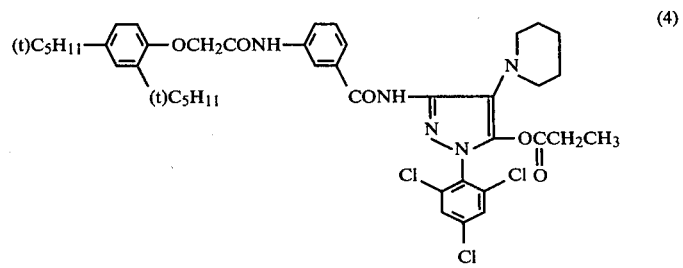

(4)

-continued
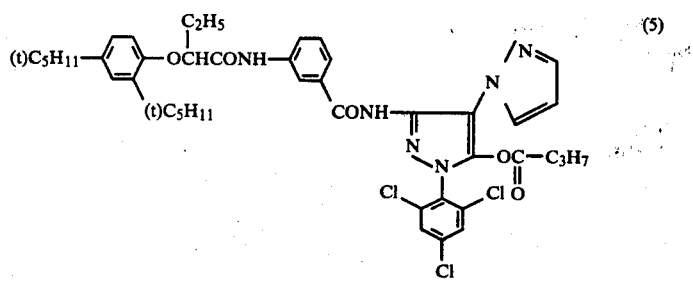 (5)
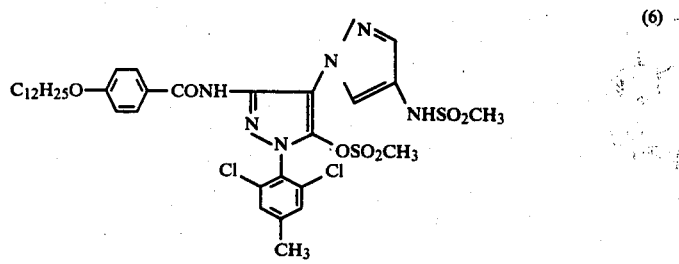 (6)
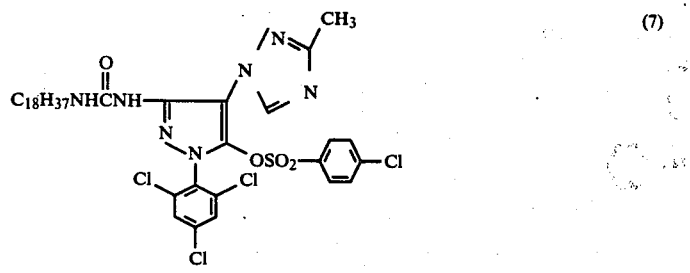 (7)
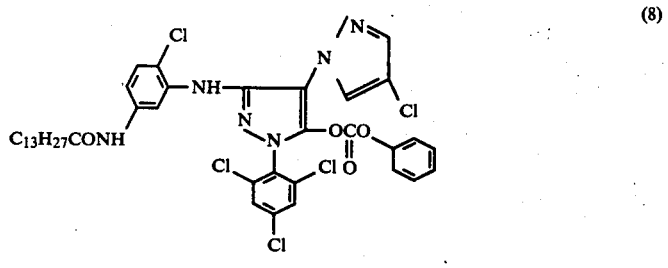 (8)
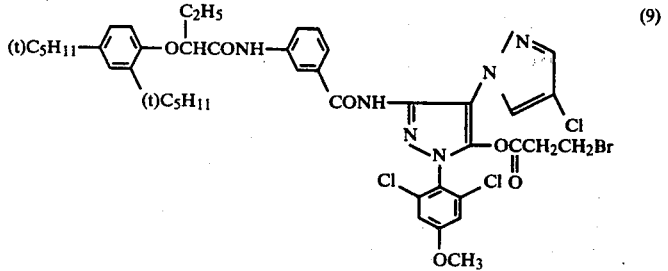 (9)
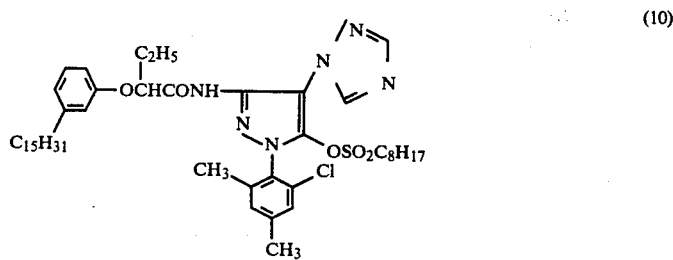 (10)

-continued
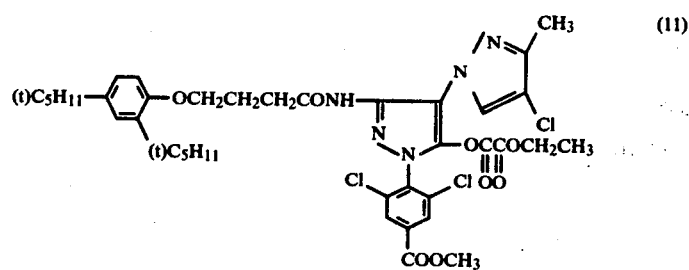 (11)
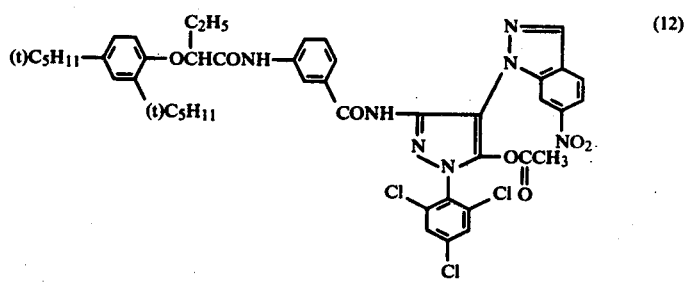 (12)
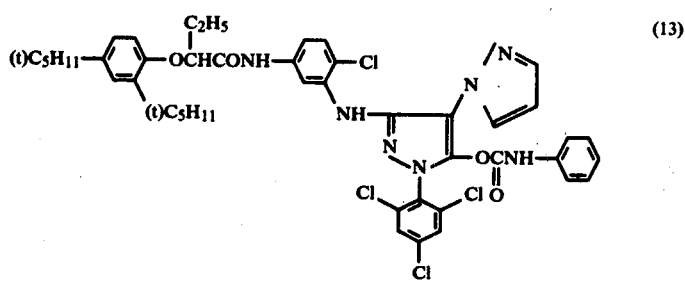 (13)
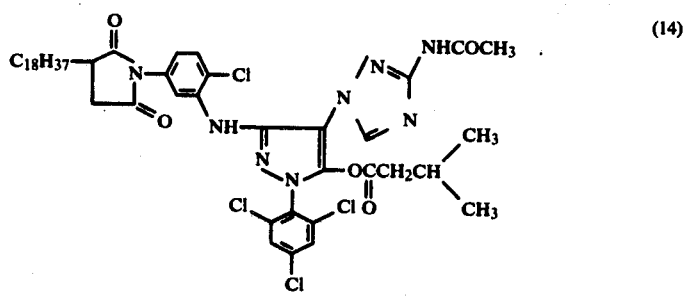 (14)
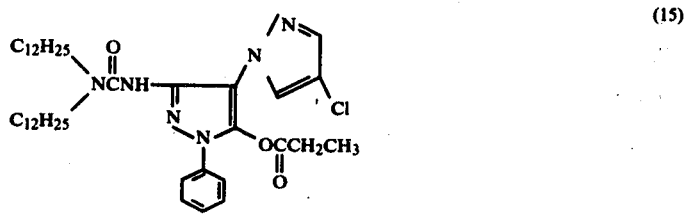 (15)
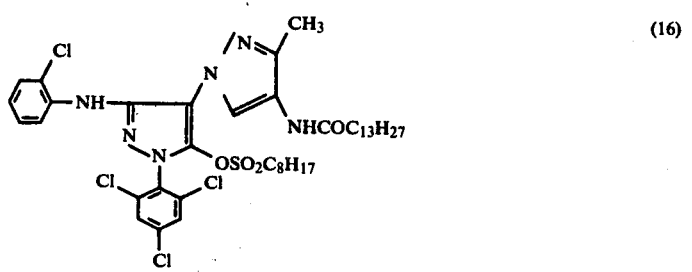 (16)

-continued
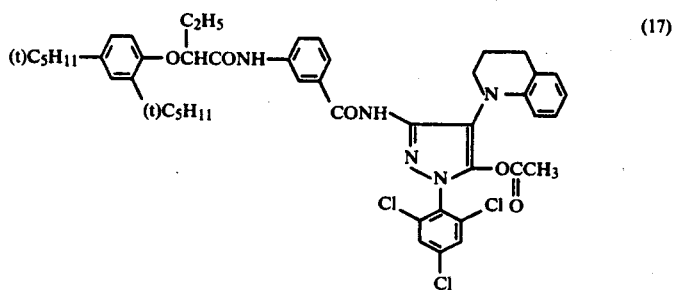
(17)
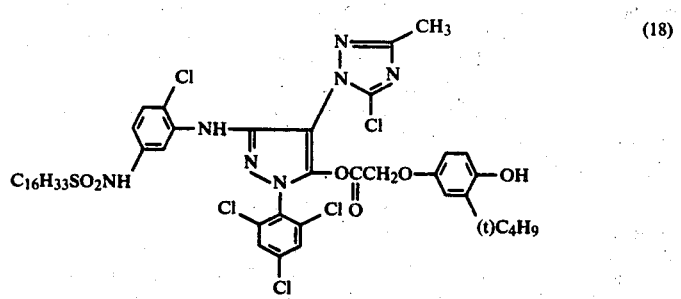
(18)
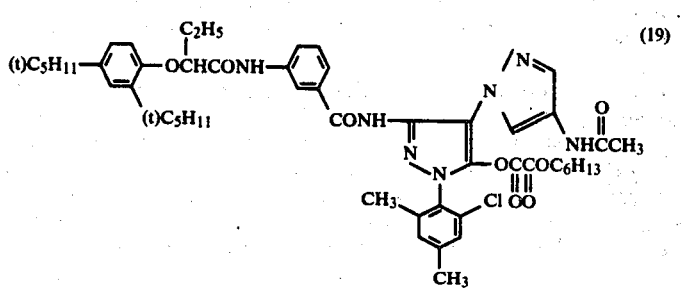
(19)
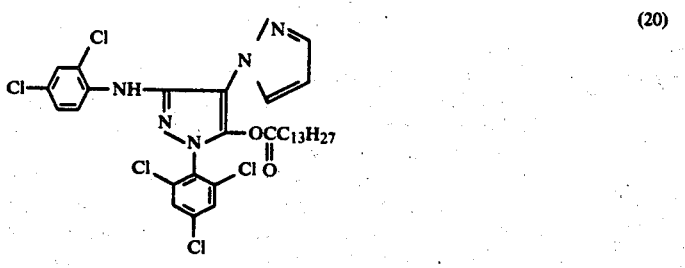
(20)
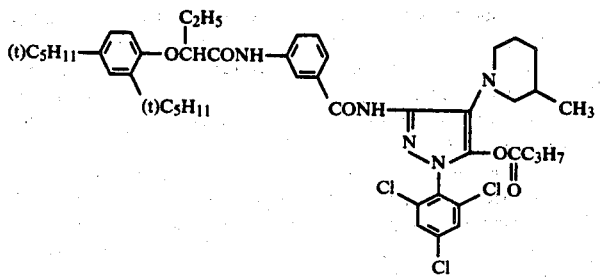
(21)
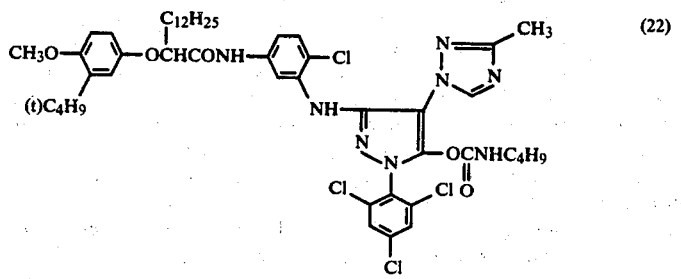
(22)

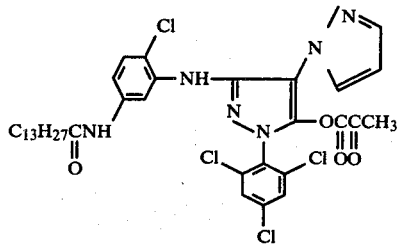

(23)

Typical examples of the synthesis of the photographic couplers of the present invention are described below.

SYNTHESIS EXAMPLE 1

Synthesis of
5-Butanoyloxy-1-(2,4,6-trichlorophenyl)-3-(2-chloro-5-tetradecanamidoanilino)-4-(1,2,4-triazol-1-yl)-1H-pyrazole [Coupler (1)]

20 g of 1-(2,4,6-trichlorophenyl)-3-(2-chloro-5-tetradecanamidoanilino)-4-(1,2,4-triazol-1-yl)-5-oxo-2-pyrazoline (prepared by the method described in U.S. Pat. No. 4,076,533) was suspended in 100 ml of acetonitrile and 3.7 g of butanoyl chloride was added to the mixture, followed by refluxing for 3 hours. After cooling to room temperature, 500 ml of ethyl acetate was added to the reaction mixture and washed several times with water. The ethyl acetate layer was dried with anhydrous sodium sulfate and concentrated. Upon crystallization of the residue from a solvent mixture of acetonitrile and benzene, 16 g of Coupler (1) was obtained. The melting point of the coupler was 89° to 95° C.

SYNTHESIS EXAMPLE 2

Synthesis of
3-{5-[2-(2,4-Di-tert-amylphenoxy)butyramido]-2-chloroanilino}-5-acetyloxy-1-(2,4,6-trichlorophenyl)-4-(1-pyrazolyl)-1H-pyrazole [Coupler (2)]

34 g of 3-{5-[2-(2,4-di-tert-amylphenoxy)butyramido]-2-chloroanilino}-1-(2,4,6-trichlorophenyl)-4-(1-pyrazolyl)-5-oxo-2-pyrazoline (prepared by the method described in German Patent Application (OLS) No. 2,536,191), 25 g of isopropenyl acetate and 0.5 g of p-toluenesulfonic acid were added to 250 ml of benzene and the mixture was refluxed for 5 hours. After the reaction, the reaction mixture was condensated under reduced pressure. Upon crystallization of the residue from a solvent mixture of benzene and hexane, 23 g of Coupler (2) was obtained. The melting point of the coupler was 102° to 108° C.

SYNTHESIS EXAMPLE 3

Synthesis of
3-{3-[2-(2,4-Di-tert-amylphenoxy)butyramido]-benzamido}-5-butanoyloxy-1-(2,4,6-trichlorophenyl)-4-(1-pyrazolyl)-1H-pyrazole [Coupler (5)]

30.6 g of 3-{3-[2-(2,4-di-tert-amylphenoxy)butyramido]benzamido}-1-(2,4,6-trichlorophenyl)-4-(1-pyrazolyl)-5-oxo-2-pyrazoline (prepared by the method described in German Patent Application (OLS) No. 2,536,191) was dissolved in 100 ml of tetrahydrofuran and 5 g of triethylamine was added. To the solution, a solution containing 3.5 g of butanoyloxy chloride dissolved in 10 ml of tetrahydrofuran was dropwise added. After the addition of the solution, the mixture was stirred for 1 hour. 500 ml of ethyl acetate was added to the reaction mixture and washed several times with water. The oil layer was dried with anhydrous sodium sulfate and concentrated. Upon crystallization of the residue from acetonitrile, 24 g of Coupler (5) was obtained. The melting point of the coupler was 63° to 68° C.

SYNTHESIS EXAMPLE 4

Synthesis of
3-{3-[2-(2,4-Di-tert-amylphenoxy)butyramido]benzamido}-5-butanoyloxy-1-(2,4,6-trichlorophenyl)-4-(3-methylpiperidin-1-yl)-1H-pyrazole [Coupler (21)]

16 g of 3-{3-[2-(2,4-di-tert-amylphenoxy)butyramido]benzamido}-1-(2,4,6-trichlorophenyl)-4-(3-methylpiperidin-1-yl)-5-oxo-2-pyrazoline (prepared by the method described in German Patent Application (OLS) No. 2,424,467) was dissolved in 100 ml of chloroform and 2.5 g of triethylamine was added. To the solution, 20 ml of a chloroform solution containing 2.6 g of butanoyloxy chloride was added dropwise at 25° C. After stirring for 1 hour, the mixture was washed several times with water. The oil layer was dried with anhydrous magnesium sulfate and concentrated. 16.5 g of Coupler (21) was obtained as an oil.

The couplers of the present invention are 2-equivalent couplers. That is, they require stoichiometrically only 2 equivalents of silver halide as an oxidizing agent to produce 1 molecule of dye.

In comparison with conventionally widely used 4-equivalent pyrazolone type couplers, the 2-equivalent couplers of the present invention require only about one-half the amount of silver halide. Thus the amount of silver halide incorporated in a light-sensitive material can be reduced to about one-half that amount required with 4-equivalent couplers. Therefore, not only is the production cost of light-sensitive materials reduced, but also light scattering is reduced as well, improving the sharpness of the images.

The magenta coupler of the present invention can be converted to an azomethine dye in a high yield through an oxidative coupling reaction wherein exposed silver halide acts as an oxidizing agent. With some conventionally used 4-equivalent couplers, a leuco dye which is an intermediate in dye formation undergoes side reactions with an azine ring or the like being formed, resulting in a low conversion yield to the dye. On the other hand, the magenta couplers of the present invention can be converted to an azomethine dye in high yield, since such a reactive intermediate is not formed. As a result, the amount of the magenta-forming coupler used in the color light-sensitive material of the present invention can be reduced, which leads to a reduction in silver halide content and in the thickness of an emulsion layer and thus to a reduction of the production cost of the light-sensitive materials, an improvement in the sharpness and facilitating rapid development processing.

The magenta coupler of the present invention has such a strong coupling activity for an oxidized aromatic primary amine color developing agent that the oxidation product of the developing agent produced upon color development is rapidly removed, thus accelerating the development of the silver halide emulsion.

Suitable amounts of the magenta coupler of the present invention are from $2 \times 10^{-3}$ to $5 \times 10^{-1}$ mol, and preferably from $1 \times 10^{-2}$ to $5 \times 10^{-1}$ mol per mol of silver (in the form of photographic silver halide).

With the magenta coupler of the present invention, the process of forming a dye is completed in a color developing bath, which enables the materials to be processed with a bleach-fixing bath containing a weak oxidizing agent such as Fe (III) chelate of ethylenediaminetetraacetic acid (EDTA) or the like and a silver complex salt-forming agent or a ferric salt (e.g., acidic ferric chloride) without using a bleaching bath containing a strong oxidizing agent such as potassium ferricyanide or potassium dichromate. This results in a shortening of the time required for the processing steps of color development and minimizes the problem of environmental pollution due to discharge of processing waste water.

The coupling position substituted magenta couplers of the present invention are less inactivated by the action of carbonyl compounds such as aldehydes or ketones. Conventionally used coupling position unsubstituted magenta couplers are often changed into compounds having a low color reaction activity such as a methylol or methylenebis compound when contacted with formaldehyde or the like in the air especially in an emulsion layer, and thus fail to attain sufficient coloration through color development. The color light-sensitive material of the present invention has the advantage that it is affected to a much lesser extent by such chemicals.

The pyrazole type magenta coupler used in the present invention has the property that, when it is used for ordinary color light-sensitive materials as described in the Examples, it has high stability over a long period of time and undergoes only a slight reduction in coloring property when stored at a low temperature under high humidity as compared with the above-described known 2-equivalent couplers. The stability of a color light-sensitive material after production is one of the most important factors in evaluating the characteristics of light-sensitive materials. Also, colored images resulting from the magenta coupler of the present invention have markedly superior heat-fastness as compared with couplers which are not substituted in the coupling position. Even in comparison with the above-described known couplers with the same pyrazolone nucleus and having other substituents in the 4-position, the colored image formed from the magenta coupler of the present invention is found to exhibit greater heat resistance.

The magenta couplers used in the present invention should be hydrolyzed prior to the coupling with an oxidation product of a developing agent in a color developer solution. Usually, the couplers are sufficiently hydrolyzed at the pH of a conventional processing solution, and can provide a high color density as shown in Examples hereinafter.

The couplers in accordance with the present invention can be employed in light-sensitive materials containing a reduced amount of silver halide, i.e., about several tenths to about 1/100 as much as the amount in ordinary color light-sensitive materials. For example, suitable amounts of silver for the photographic materials of the present invention are $1 \times 10^{-3}$ to $3 \times 10^{-1}$ mol/m$^2$. With color light-sensitive materials containing a reduced amount of silver halide, suitable color images can be obtained by, for example, halogenation-bleaching silver deposits formed by color development and again conducting color development to increase the amount of dye produced (for example, U.S. Pat. Nos. 2,623,822, 2,814,565, etc.), or by employing a development processing utilizing color intensification using peroxides or cobalt complex salts to increase the amount of dye produced (for example, West German Patent Application (OLS) No. 2,357,694, U.S. Pat. Nos. 3,674,490, 3,761,265, West German Patent Application (OLS) Nos. 2,044,833, 2,056,359, 2,056,360, 2,226,770, Japanese Patent Application (OPI) Nos. 9728/73 and 9729/73, etc.).

The 2-equivalent magenta coupler of this invention can be used together with other magenta couplers, as described, for instance, in U.S. Pat. Nos. 2,439,098, 2,369,489, 2,600,788, 3,558,319, 2,311,081, 3,419,391, 3,214,437, 3,006,759, 2,725,292, 3,408,194, 2,908,573, 3,519,429, 3,615,506, 3,432,521, 3,152,896, 3,062,653, 3,582,322, 2,801,171, 3,311,476, 3,907,571, 3,935,015, 3,960,571, 4,163,670, British Pat. Nos. 956,261, 1,420,637, French Patent 7,417,395, Japanese Patent Publication Nos. 2016/69 and 19032/71, with the magenta-colored couplers, as described in U.S. Pat. Nos. 2,983,608, 2,455,170, 2,725,292, 3,005,712, 3,519,429, and 2,688,539, British Pat. Nos. 800,262 and 1,044,778, and Belgian Pat. No. 676,691, with the so-called development inhibitor releasing type couplers capable of imagewise releasing development inhibiting compounds at development, such as, for instance, the monothio type couplers as described in U.S. Pat. Nos. 3,227,550 and 3,227,554 and British Pat. No. 953,454, the o-aminophenylazo type couplers as described in U.S. Pat. No. 3,148,062, and the couplers as described in Japanese Patent Publication No. 8750/72 and German Patent Application (OLS) No. 2,163,811, and also with the hydroquinone releasing development inhibiting compounds as described in U.S. Pat. No. 3,297,445 and British Pat. No. 1,058,606.

One or more of the above-described couplers and the like can be employed in the same layer to achieve the properties required for a particular light-sensitive material and, of course, the same compound can be incorporated in two or more different layers. In general, the couplers are coated at a coverage of about $1 \times 10^{-4}$ to $5 \times 10^{-3}$ mol/m$^2$, preferably $3 \times 10^{-4}$ to $2 \times 10^{-3}$ mol/m$^2$.

The light-sensitive material of the present invention advantageously contains a p-substituted phenol derivative in an emulsion layer or an adjacent layer for the purpose of improving the light fastness of the magenta dye formed or of preventing yellowing or print-out of a coupler remaining in the unexposed areas, color fogging, or the like. Particularly effective p-substituted phenol derivatives are the hydroquinone derivatives described in U.S. Pat. Nos. 2,360,290, 2,418,613, 2,675,314, 2,701,197, 2,704,713, 2,710,801, 2,728,659, 2,732,300, 2,735,765, 2,816,038; the gallic acid derivatives as described in U.S. Pat. Nos. 3,457,079, 3,069,262 and Japanese Patent Publication No. 13496/68; the p-alkoxyphenol derivatives as described in U.S. Pat. No. 2,735,765 and Japanese Patent Application (OPI) No.

4738/72; and p-hydroxyphenol derivatives as described in U.S. Pat. Nos. 3,432,300, 3,573,050, 3,574,627 and Japanese Patent Publication No. 20977/74.

The silver halide emulsion which can be used in this invention can be suitably selected from various kinds of photographic emulsions depending on the end-use purposes of the photographic materials. Suitable silver halides which can be used in this invention include silver chloride, silver chlorobromide, silver bromide, silver iodobromide, and silver chloroiodobromide. Also, suitable binders for the silver halide emulsions which can be used in this invention are gelatin, gelatin derivatives (e.g., the acrylated gelatin as described in U.S. Pat. No. 3,118,766 and the graft gelatin having as the branch component a vinyl monomer such as acrylic acid as described in U.S. Pat. No. 2,831,767), casein, albumin, agar agar, sodium alginate, starch, cellulose derivatives (e.g., carboxymethyl cellulose and hydroxyethyl cellulose), vinyl alcohol, vinylpyrrolidone, polyacrylamide, and the like.

The silver halide emulsions used in this invention can be prepared by a single jet method, a double jet method, a control double jet method, and further the halogen conversion method as described in British Pat. No. 635,841 and U.S. Pat. No. 3,622,318.

The silver halide emulsion used in this invention can be sensitized by the natural sensitizers present in gelatin, by a sulfur sensitizer, by a reductive sensitizer, and by a noble metal salt using conventional techniques.

The silver halide emulsion can contain an anti-fogging agent or a stabilizer such as 1-phenyl-5-mercaptotetrazole, 5-methyl-7-hydroxy-1,3,4,7a-tetraazaindene, etc. Also, the silver halide emulsion can contain a sensitizing dye such as a cyanine dye, a merocyanine dye, etc. The silver halide emulsion can contain a coating aid such as saponin, polyethylene glycol monolauryl ether, etc. Furthermore, the silver halide emulsion can contain a thickener such as polystyrenesulfonic acid, etc., an ultraviolet absorber such as 2-(2-hydroxy-3,5-disecbutylphenyl)-5-methoxybenzotriazole, 4-methoxy-α-cyanocinnamic acid-n-dodecyl ester, etc., an antioxidant or a reducing agent such as sodium bisulfite, ascorbic acid, aminophenols, pyrogallols, gallic acids, catechols, resorcinols, and dihydroxynaphthalenes, and an irradiation preventing dye such as an oxonol dye and a styryl dye, and other conventional photographic additives, if desired.

A photographic light-sensitive material according to the present invention comprises a support having thereon a silver halide emulsion layer containing a 2-equivalent magenta coupler in accordance with the present invention. One embodiment of a photographic light-sensitive material according to this invention comprises a multilayered, multicolored photographic light-sensitive material comprising a support having thereon a blue-sensitive halide emulsion layer containing a yellow coupler (that is, a coupler that forms a yellow dye), a green-sensitive silver halide emulsion layer containing a magenta color-forming coupler in accordance with the present invention, and a red-sensitive silver halide emulsion layer containing a cyan coupler (that is, a coupler that forms a cyan dye). Known blue-sensitive silver halide emulsions and the red-sensitive silver halide emulsions can be appropriately used. Open-chain type ketomethylene compounds represented by benzoylacetanilides and pivaloylacetanilides can advantageously be used as yellow color-forming couplers. Phenolic or naphtholic compounds can advantageously be used as cyan color-forming couplers. Such color-forming couplers can contain a coupling off group on the carbon atom of the coupling position, and are desirably non-diffusible.

The photographic light-sensitive material of the present invention can have, in addition to the aforesaid silver halide emulsion layers, light-insensitive auxiliary layers such as a protective layer, a filter layer, intermediate layers, an antihalation layer, and a backing layer.

The hydrophilic polymer material, particularly gelatin constituting the layers of the photographic light-sensitive material of the present invention can be hardened by various cross-linking agents. For example, although an inorganic compound such as a chromium salt and a zirconium salt, and an aldehyde type cross-linking agent such as mucochloric acid, 2-phenoxy-3-chloromalealdehydic acid, etc., as described in Japanese Patent Publication No. 1872/71 can be used, a non-aldehyde type cross-linking agent, for example, a polyepoxy compound as described in Japanese Patent Publication No. 7133/59, a poly(1-aziridinyl) compound as described in Japanese Patent Publication No. 8790/62, an active halogen compound as described in U.S. Pat. Nos. 3,362,827 and 3,325,287, etc., are particularly useful.

In the photographic light-sensitive materials of the present invention, any materials usually used as supports for photographic light-sensitive materials can be suitably used. For instance, preferred examples of such supports are cellulose ester films such as cellulose nitrate films, cellulose acetate films, etc., polyester films such as polyethylene terephthalate films, etc., polyvinyl chloride films, polyvinyl acetal films, polystyrene films, polycarbonate films, polyamide films such as nylon films, baryta-coated papers, α-olefin polymer-coated papers, and so forth.

The photographic light-sensitive material of the present invention can be suitably used for various purposes such as color positive films, color negative films, color reversal films, color photographic printing papers, and so forth.

The color photographic light-sensitive material of the present invention provides magenta color images having excellent spectral properties and image fastness when imagewise exposed in a conventional manner and processed using conventional color processing steps. The main color processing steps are color development, bleach, and fix and if desired a wash step can be inserted between each of the steps.

A useful color developer which can be used for developing the color photographic material of this invention is an alkaline aqueous solution containing a color developing agent, and having a pH of from about 9.5 to 12.2. Examples of color developing agents which can be used in the color developer include conventional primary aromatic amine color developing agents such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-diethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline), and p-aminophenols (e.g., 4-aminophenol, 2,6-dichloro-4-aminophenol, 2-bromo-4-aminophenol, and 2,6-diiodo-4-aminophenol).

The color developer can contain further conventional additives such as, for instance, an alkali metal sulfite, an alkali metal carbonate, an alkali metal bisulfite, a bromide, an iodide, an alkaline buffer, etc. Furthermore, if desired, the color developer can contain a dye forming coupler, a competitive coupler, an anti-foggant, a hardening agent, an antioxidant, a thickener, and so forth.

Some of the advantages of the present invention are as follows.

(1) Since the amount of silver necessary for obtaining the same magenta color image density can be reduced, and also the amount of oil for dissolving the coupler can be reduced due to the good solubility of the coupler according to the present invention, the thickness of the light-sensitive layer containing the coupler can be reduced, thus improving the sharpness of the images obtained.

(2) Silver halide color photographic light-sensitive materials having excellent storage stability and high sensitivity can be obtained using the coupler of the present invention.

(3) Magenta couplers stable to chemicals such as formalin or acetone can be obtained.

(4) The heat fastness of the magenta color images produced using the coupler of the present invention is improved.

(5) The production cost can be reduced through the reduction in the amount of silver halide necessary.

(6) Color images with less fog and stain and with excellent other photographic properties can be obtained.

The light-sensitive materials of the present invention having the above-described advantages are extremely useful in the field of color photography.

The present invention will now be illustrated in more detail by the following non-limiting examples of preferred embodiments of the present invention.

EXAMPLE 1

A solution, prepared by heating at 60° C. and dissolving a mixture comprising 21.0 g of Coupler (1) in accordance with the present invention, 20 ml of dioctyl butyl phosphate and 60 ml of ethyl acetate, was added to 250 ml of a 60° C. aqueous solution containing 2.5 g of gelatin and 0.75 g of sodium dodecylbenzenesulfonate. The resulting solution was mechanically vigorously stirred using a homogenizer to obtain a coupler emulsion dispersion. This emulsion dispersion was mixed with 200 g of a photographic emulsion containing $11.2 \times 10^{-2}$ mol of silver chlorobromide (silver bromide: 45 mol%, silver chloride: 55 mol%) and 20 g of gelatin. Then, 10 ml of a 3% acetone solution of triethylenephosphoramide was added thereto as a hardener and, after adjusting the final pH to 6.5, the solution was coated on a cellulose triacetate film support in a dry thickness of 4.5μ (Film A). This film contained $1.53 \times 10^{-3}$ mol/m$^2$ of Coupler (1) and $6.2 \times 10^{-3}$ mol/m$^2$ of silver chlorobromide.

22.9 g of Coupler (2), 22.7 g of Coupler (4) and 23.4 g of Coupler (5) in accordance with the present invention and, as comparison couplers, 19.6 g of 1-(2,4,6-trichlorophenyl)-3-{3-[2-(2,4-di-tert-amylphenoxy)-butyramido]benzamido}-5-oxo-2-pyrazoline (Coupler L), 19.1 g of 3-(2-chloro-5-tetradecanamidoanilino)-1-(2,4,6-trichlorophenyl)-4-(1,2,4-triazol-1-yl)-5-oxo-2-pyrazoline (Coupler M), 18.8 g of 3-{5-[2-(2,4-di-tert-amylphenoxy)butyramido]-2-chloroanilino}-1-(2,4,6-trichlorophenyl)-5-oxo-2-pyrazoline (Coupler N), 29.7 g of 3-[3-(2,4-di-tert-amylphenoxyacetamido)benzamido]-5-butyryloxy-1-(2,4,6-trichlorophenyl)-4-(3-dodecylcarbamoylphenylthio)-1H-pyrazole (Coupler O), 32.6 g of 3-{3-[2-(2,4-di-tert-amylphenoxy)-butyramido]benzamido}-5-octanoyloxy-4-(4-tetradecylcarbamoylphenylthio)-1-(2,4,6-trichlorophenyl)-1H-pyrazole (Coupler P) and 27.7 g of 5-butyryloxy-5-(2-chloro-5-dodecylcarbamoylanilino)-4-(3-dodecylcarbamoylphenylthio)-1-(2,4,6-trichlorophenyl)-1H-pyrazole (Coupler Q) were dispersed respectively in place of the above-described Coupler (1) in the same manner as described above, mixed with 200 g of a silver halide emulsion having the same composition as above with respect to Coupler (2), Coupler (4), Coupler (5), Coupler (M), Coupler (O), Coupler (P) and Coupler (Q) and with 400 g of a silver halide emulsion having the same composition as above with respect to Coupler (L) and Coupler (N) respectively, and coated on a film. The dry thickness of the layers and coated amounts of coupler and silver chlorobromide emulsion on the films were shown in Table 1 below.

These films were subjected to stepwise exposure and the following development processing steps.

| Color Development Processing: | | |
|---|---|---|
| 1. Color development | 38° C. | 3 min 15 sec |
| 2. Bleaching | " | 6 min 30 sec |
| 3. Washing with water | " | 2 min |
| 4. Fixing | " | 4 min |
| 5. Washing | " | 4 min |

The processing solutions used had the following compositions.

| Color Development Solution | |
|---|---|
| 4-Amino-3-methyl-N-ethyl-N-β-hydroxyethylaniline Sesquisulfate | 5 g |
| Sodium Sulfite (anhydrous) | 5 g |
| Hydroxylamine Sulfate | 2 g |
| Potassium Carbonate | 30 g |
| Potassium Hydrogen Carbonate | 1.2 g |
| Potassium Bromide | 1.2 g |
| Sodium Chloride | 0.2 g |
| Trisodium Nitrilotriacetate | 1.2 g |
| Water to make | 1 l |
| | (pH = 10.1) |
| Bleaching Solution | |
| Ferric Salt of Ethylenediaminetetraacetate | 100 g |
| Disodium Ethylenediaminetetraacetate | 10 g |
| Potassium Bromide | 150 g |
| Hydroxylamine Acetate | 10 g |
| Water to make | 1 l |
| | (pH = 6.0) |
| Fixing Solution | |
| Ammonium Thiosulfate | 150 g |
| Sodium Sulfite | 10 g |
| Sodium Hydrogen Sulfite | 2.5 g |
| Water to make | 1 l |
| | (pH = 6.0) |

After processing, the optical density of these film samples was measured using green light. As a result, the photograhic properties as shown in Table 1 were obtained.

TABLE 1

| Film | Coupler | Coated Amount (mol/m²) Coupler (M) | Coated Amount (mol/m²) Ag (M) | Ag/Coupler (molar ratio) | Film Thickness | Fog | Gamma | Relative Sensitivity | Maximum Color Density |
|---|---|---|---|---|---|---|---|---|---|
| A | (1) | $1.53 \times 10^{-3}$ | $6.2 \times 10^{-3}$ | 4 | 4.5 | 0.03 | 4.2 | 201 | 3.72 |
| B | (2) | $1.55 \times 10^{-3}$ | $6.2 \times 10^{-3}$ | 4 | 4.4 | 0.03 | 4.1 | 210 | 3.59 |
| C | (4) | $1.54 \times 10^{-3}$ | $6.3 \times 10^{-3}$ | 4 | 4.6 | 0.03 | 4.2 | 205 | 3.62 |
| D | (5) | $1.52 \times 10^{-3}$ | $6.1 \times 10^{-3}$ | 4 | 4.6 | 0.03 | 4.3 | 186 | 3.59 |
| E | (L) | $1.53 \times 10^{-3}$ | $12.4 \times 10^{-3}$ | 8 | 5.2 | 0.03 | 2.0 | 100 | 2.05 |
| F | (M) | $1.59 \times 10^{-3}$ | $6.4 \times 10^{-3}$ | 4 | 4.5 | 0.01 | 1* | 1* | 1* |
| G | (N) | $1.52 \times 10^{-3}$ | $12.2 \times 10^{-3}$ | 8 | 5.3 | 0.03 | 1.9 | 99 | 2.00 |
| H | (O) | $1.51 \times 10^{-3}$ | $6.0 \times 10^{-3}$ | 4 | 4.4 | 0.03 | 1.5 | 75 | 1.98 |
| I | (P) | $1.55 \times 10^{-3}$ | $6.2 \times 10^{-3}$ | 4 | 4.5 | 0.03 | 1.6 | 73 | 1.94 |
| J | (Q) | $1.54 \times 10^{-3}$ | $6.2 \times 10^{-3}$ | 4 | 4.6 | 0.04 | 1.9 | 134 | 2.35 |

1* No color formation due to crystallization of the couplers in the film.

The results in Table 1 show that the coupler according to the present invention provides higher sensitivity, higher gradation (gamma) and higher maximum color density than the 4-equivalent couplers even when the ratio of silver halide/coupler was reduced to about ½. Also, in comparison with Films H, I and J, the coupler according to the present invention provided higher sensitivity, higher gradation and higher maximum color density than Couplers O, P and Q having an arylthio group as a coupling off group (included within the scope of Japanese Patent Application (OPI) No. 80744/79). Furthermore, in comparison with Coupler (1) according to the present invention, the 5-pyrazolone type magenta coupler (M) had a low solubility and crystallized just after the coating had been applied to. These facts indicate that couplers according to the present invention represent an improvement in terms of solubility considerations.

EXAMPLE 2

A solution obtained by dissolving 8.8 g of Coupler (1) of the present invention, 10 ml of tricresyl phosphate and 20 ml of ethyl acetate with heating at 60° C. was added to 80 ml of an aqueous solution containing 8 g of gelatin, 0.20 g of sodium dodecylbenzenesulfonate at 60° C. The solution mixture was stirred with a homogenizer to prepare a coupler dispersion. The coupler dispersion was mixed with 100 g of a green-sensitive photographic emulsion containing $4.70 \times 10^{-2}$ mol of silver chlorobromide (50 mol% silver chloride) and 9 g of gelatin, and 5 ml of a 3% acetone solution of triethylenephosphoramide was further added thereto as a hardening agent. After adjusting the pH to 7.0, the dispersion was coated onto a paper sheet having polyethylene coated thereon in a thickness of 3.4 microns (dry thckness; hereafter all thicknesses given are dry thicknesses). Gelatin was coated thereon (using a 2% gelatin aqueous solution) in a thickness of 1 micron to prepare a color print paper (Sample S).

Color print papers were prepared in a manner similar to the preparation of Sample S except that Couplers (2) and (13) according to the present invention were employed in lieu of Coupler (1) and Comparison Couplers (O), (P) and (Q) and 3-{5-[2-(2,4-di-tert-amylphenoxy)-butyramido]-2-chloroanilino}-1-(2,4,6-trichlorophenyl)-4-pyrazolyl-5-oxo-2-pyrazoline (Coupler R) were employed as magenta color image-forming couplers for comparison, respectively. Samples T and U were prepared from Couplers (2) and (13), and Samples V, W, X and Y were prepared from Comparison Couplers (O), (P), (Q) and (R), respectively.

These samples were allowed to stand at 50° C. for 2 weeks. On the other hand, the same samples were allowed to stand at 5° C. for 2 weeks. Each of these samples was exposed to green light using a step wedge and processed in the following development processings.

| Processing Step | Temperature | Time |
|---|---|---|
| 1. Color Development | 30° C. | 4 min |
| 2. Bleach-Fixing | " | 2 min |
| 3. Water Washing | " | 2 min |
| 4. Stabilizing | " | 2 min |

The processing solutions used had the following compositions:

| Composition of Color Developer | |
|---|---|
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (nitrate) | 0.02 g |
| Sodium Hydroxide | 4 g |
| Benzyl Alcohol | 15.8 ml |
| Diethylene Glycol | 20 ml |
| 4-(N-Ethyl-N-β-methanesulfonamido-ethyl)amino-2-methylaniline Sesquisulfate | 8 g |
| Water to make | 1 l |
| Composition of Bleach-Fixing Solution | |
| Ferric Salt of Ethylenediaminetetraacetate | 45 g |
| Ammonium Thiocyanate | 10 g |
| Sodium Sulfite | 10 g |
| Ammonium Thiosulfate (60% aq. soln.) | 100 ml |
| Tetrasodium Ethylenediaminetetraacetate | 5 g |
| Water to make | 1 l |
| Composition of Stabilizing Bath | |
| Tartaric Acid | 10 g |
| Zinc Sulfate | 10 g |
| Sodium Metaborate | 20 g |
| Water to make | 1 l |

After the processing described above, optical densities of these film samples for green light were measured to obtain the color densities as shown in Table 2.

TABLE 2

| | | Comparison of Color Density after Storage | | |
|---|---|---|---|---|
| | | Maximum Color Density Exposed and Processed after Storage | | Density Reduction Rate (%) |
| Print Paper | Coupler | at 5° C. for 2 Weeks | at 50° C. for 2 Weeks | Dm(5° C.)−Dm(50° C.) / Dm(5° C.) |
| S | (1) | 2.52 | 2.48 | 1.6 |
| T | (2) | 2.55 | 2.46 | 3.5 |
| U | (13) | 2.52 | 2.49 | 1.2 |
| V | (O) | 1.72 | 1.58 | 8.1 |
| W | (P) | 1.93 | 1.83 | 5.2 |
| X | (Q) | 2.21 | 1.96 | 11.3 |
| Y | (R) | 2.50 | 1.62 | 35.2 |

The results shown in Table 2 indicate that couplers according to the present invention are extremely stable and undergo little decomposition. Thus, print papers containing these couplers provide almost same color densities (as that in the case of storage at low temperature (5° C.)) even they have been subjected to the heated storage (50° C.). Furthermore, the couplers according to the present invention have excellent color forming properties in the print paper samples in comparison with Comparison Couplers (O), (P) and (Q), as shown in Example 1.

While the invention has been described in detail and with reference to specific embodiments thereof, it will be apparent to one skilled in the art that various changes and modifications can be made therein without departing from the spirit and scope thereof.

What is claimed is:

1. A process for forming a color photographic image comprising processing a silver halide color photographic light-sensitive material in the presence of a magenta coupler represented by the formula (I)

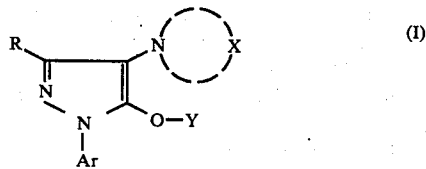

wherein R represents an acylamino group, an anilino group or a ureido group; Ar represents a substituted or unsubstituted aryl group; the

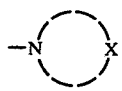

group forms a heterocyclic group represented by the formula (IV), (V) or (VI)

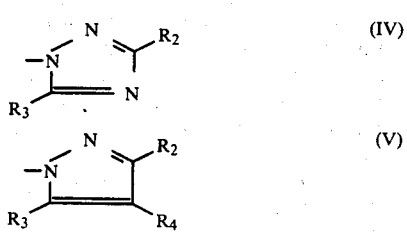

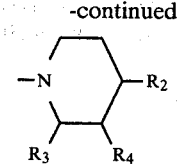

wherein $R_2$, $R_3$ and $R_4$ each represents a hydrogen atom, a halogen atom, a nitro group, a nitroso group, an acylamino group, a sulfonamido group, a urethane group, a diacylamino group, a ureido group, an alkylthio group, an alkylsulfonyl group, an alkoxy group, an alkylcarbonyl group, an alkoxycarbonyl group, a sulfamoyl group, a sulfo group, a hydroxy group, an acyloxycarbonyl group, an arylthio group, an aryloxy group, a carbamoyl group, a cyano group, an anilino group, an arylsulfonyl group, an aryloxycarbonyl group, an alkyl group having from 1 to 35 carbon atoms, an alkenyl group, a cycloalkyl group, an aralkyl group, an aryl group or a heterocyclic group; or $R_2$ and $R_4$ together, or $R_3$ and $R_4$ together for a ring; and Y represents an acyl group or a sulfonyl group.

2. A process as in claim 1, wherein R represents an acylamino group selected from the group consisting of an acetamido group, a benzamido group, a 3-[α-(2,4-di-tert-amylphenoxy)butyramido]benzamido group, a 3-[α-(2,4-di-tert-amylphenoxy)acetamido]benzamido group, a 3-[α-(3-pentadecylphenoxy)butyramido]benzamido group, an γ-(2,4-di-tert-amylphenoxy)butyramido group, and an α-(3-pentadecylphenoxy)butyramido group.

3. A process as in claim 1, wherein R represents an anilino group selected from the group consisting of an anilino group, a 2-chloroanilino group, a 2,4-dichloroanilino group, a 2-chloro-5-tetradecanamidoanilino group, a 2-chloro-5-(2-octadecenylsuccinimido)anilino group, a 2-chloro-5-[α-(3-tert-butyl-4-hydroxy)tetradecanamido]anilino group, a 2-chloro-5-tetradecyloxycarbonylanilino group, a 2-chloro-5-(N-tetradecylsulfamoyl)anilino group, and a 2,4-dichloro-5-tetradecyloxyanilino group.

4. A process as in claim 1, wherein R represents a ureido group selected from the group consisting of a 3-[(2,4-di-tertamylphenoxy)acetamido]phenylureido group, a phenylureido group, a methylureido group, an octadecylureido group, and a 3-tetradecanamidophenylureido group.

5. A process as in claim 1, wherein Ar is an aryl group having one or more substituents selected from the group consisting of an alkyl group, an alkenyl group, a cycloalkyl group, an aralkyl group, a cycloalkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group and a mercapto group.

6. A process as in claim 1, wherein Ar represents a phenyl group in which at least one of the ortho-positions is substituted with an alkyl group, an alkoxy group or a halogen atom.

7. A process as in claim 1, wherein said —O—Y group is represented by the formula (II) or (III)

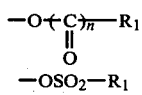

wherein $R_1$ represents an alkyl group having from 1 to 18 carbon atoms, an alkenyl group, a cycloalkyl group, an aralkyl group, an alkylamino group, a dialkylamino group, an anilino group, an alkoxy group or an aryloxy group; and n represents 1 or 2.

8. A process as in claim 7, wherein $R_1$ may have one or more substituents selected from the group consisting of a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamide group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group.

9. A process as in claim 1, wherein said magenta coupler is present in a silver halide color photographic light-sensitive material.

10. A process as in claim 1 which comprises bleach-fixing said color photographic material after color development.

11. A color photographic light-sensitive material comprising a support having thereon at least one silver halide emulsion layer, and including at least one layer containing a magenta coupler represented by the formula (I)

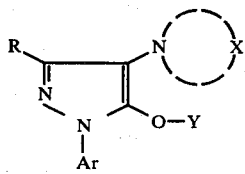

wherein R represents an acylamino group, an anilino group or a ureido group; Ar represents a substituted or unsubstituted aryl group; the

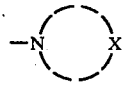

group forms a heterocyclic group represented by the formula (IV), (V) or (VI)

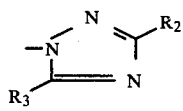

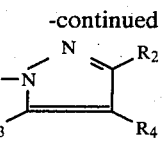

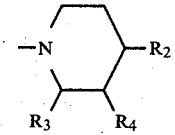

wherein $R_2$, $R_3$ and $R_4$ each represents a hydrogen atom, a halogen atom, a nitro group, a nitroso group, an acylamino group, a sulfonamido group, a urethane group, a diacylamino group, a ureido group, an alkylthio group, an alkylsulfonyl group, an alkoxy group, an alkylcarbonyl group, an alkoxycarbonyl group, a sulfamoyl group, a sulfo group, a hydroxy group, an acyloxycarbonyl group, an arylthio group, an aryloxy group, a carbamoyl group, a cyano group, an anilino group, an arylsulfonyl group, an aryloxycarbonyl group, an alkyl group having from 1 to 35 carbon atoms, an alkenyl group, a cycloalkyl group, an aralkyl group, an aryl group or a heterocyclic group; or $R_2$ and $R_4$ together, or $R_3$ and $R_4$ together form a ring; and Y represents an acyl group or a sulfonyl group.

12. A color photographic light-sensitive material as in claim 11, wherein R represents an acylamino group selected from the group consisting of an acetamido group, a benzamido group, a 3-[α-(2,4-di-tert-amylphenoxy)butyramido]benzamido group, a 3-[α-(2,4-di-tert-amylphenoxy)acetamido]benzamido group, a 3-[α-(3-pentadecylphenoxy)butyramido]benzamido group, an γ-(2,4-di-tert-amylphenoxy)butyramido group, and an α-(3-pentadecylphenoxy)butyramido group.

13. A color photographic light-sensitive material as in claim 11, wherein R represents an anilino group selected from the group consisting of an anilino group, a 2-chloroanilino group, at 2,4-dichloroanilino group, a 2-chloro-5-tetradecanamidoanilino group, a 2-chloro-5-[2-octadecenylsuccinimido]anilino group, a 2-chloro-5-[α-(3-tert-butyl-4-hydroxy)tetradecanamido]anilino group, a 2-chloro-5-tetradecyloxycarbonylanilino group, a 2-chloro-5-(N-tetradecylsulfamoyl)anilino group, and a 2,4-dichloro-5-tetradecyloxyanilino group.

14. A color photographic light-sensitive material as in claim 11, wherein R represents a ureido group selected from the group consisting of a 3-[(2,4-di-tert-amylphenoxy)acetamido]phenylureido group, a phenylureido group, a methylureido group, an octadecylureido group, or a 3-tetradecanamidophenylureido group.

15. A color photographic light-sensitive material as in claim 11, wherein Ar is an alkyl group having one or more substituents selected from the group consisting of an alkyl group, an alkenyl group, a cycloalkyl group, an aralkyl group, a cycloalkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N- alkylanilino group, an N-arylanilino group, an N-acylanilino group, a hydroxy group and a mercapto group.

16. A color photographic light-sensitive material as in claim 11, wherein Ar represents a phenyl group in which at least one of the ortho-positions is substituted with an alkyl group, an alkoxy group or a halogen atom.

17. A color photographic light-sensitive material as in claim 11, wherein said —O—Y group is represented by the formula (II) or (III)

wherein $R_1$ represents an alkyl group having from 1 to 18 carbon atoms, an alkenyl group, a cycloalkyl group, an aralkyl group, an alkylamino group, a dialkylamino group, an anilino group, an alkoxy group or an aryloxy group; and n represents 1 or 2.

18. A color photographic light-sensitive material as in claim 17, wherein $R_1$ may have one or more substituents selected from the group consisting of a halogen atom, a nitro group, a cyano group, a thiocyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group.

19. A color photographic light-sensitive material as in claim 11, wherein said magenta coupler is present in a silver halide emulsion layer.

20. A color photographic light-sensitive material as in claim 19, wherein said silver halide emulsion layer is a green-sensitive silver halide emulsion layer.

21. A color photographic light-sensitive material as in claim 20 comprising a support having thereon at least one blue-sensitive silver halide emulsion layer containing a yellow color forming coupler, said green-sensitive silver halide emulsion layer containing said magenta color forming coupler and a red-sensitive silver halide emulsion layer containing a cyan color forming coupler.

22. A color photographic light-sensitive material as in claim 21, wherein said color forming couplers are non-diffusible.

23. A color photographic light-sensitive material as in claim 11, wherein Ar or R contains a hydrophobic group containing at least 8 carbon atoms.

24. A color photographic light-sensitive material as in claim 11, 12, 13, 14, 15, 16, 17, 18, 19, 20, 21, 22, or 23, wherein the concentration of the magenta coupler is from $2 \times 10^{-3}$ to $5 \times 10^{-1}$ mol per mol of silver.

25. A color photographic light-sensitive material as in claim 11, 12, 13, 14, 15, 16, 17, 18, 19, 20, 21, 22, or 23, wherein the concentration of the magenta coupler is from $1 \times 10^{-2}$ to $5 \times 10^{-1}$ mole per mol of silver.

* * * * *